United States Patent
Edwardsen et al.

(10) Patent No.: US 6,749,572 B2
(45) Date of Patent: Jun. 15, 2004

(54) TRANSESOPHAGEAL ULTRASOUND PROBE HAVING A ROTATING ENDOSCOPE SHAFT

(75) Inventors: Stephen Dodge Edwardsen, Sandefjord (NO); Dag Jordfald, Horten (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/317,158

(22) Filed: Dec. 10, 2002

(65) Prior Publication Data

US 2003/0092997 A1 May 15, 2003

Related U.S. Application Data

(63) Continuation of application No. 09/681,296, filed on Mar. 14, 2001, now abandoned.

(51) Int. Cl.[7] .................................................. A61B 8/14
(52) U.S. Cl. ........................................ 600/459; 600/462
(58) Field of Search ................................ 600/407–471, 600/101, 476, 564, 562, 104; 601/2, 3; 606/114, 139, 148, 1, 205, 15, 170, 174; 604/57; 607/98, 122; 73/620–633; 367/7, 11, 130, 138; 128/898, 916

(56) References Cited

U.S. PATENT DOCUMENTS

| | | | | |
|---|---|---|---|---|
| 5,211,176 A | * | 5/1993 | Ishiguro et al. | 600/463 |
| 5,215,092 A | * | 6/1993 | Wray | 600/445 |
| 5,388,584 A | * | 2/1995 | King | 600/462 |
| 5,413,107 A | * | 5/1995 | Oakley et al. | 600/463 |
| 5,479,929 A | * | 1/1996 | Cooper et al. | 600/459 |
| 5,634,466 A | * | 6/1997 | Gruner | 600/459 |
| 5,738,631 A | * | 4/1998 | Konstorum | 600/148 |

* cited by examiner

Primary Examiner—Ali Imam
(74) Attorney, Agent, or Firm—McAndrews, Held & Malloy, Ltd.; Peter J. Vogel; Michael A. Dellapenna

(57) ABSTRACT

A transesophageal ultrasound probe for imaging internal structures via an imaging element located on the distal end of a rotating endoscope shaft. The probe includes a rotating endoscope having an imaging element mounted on the distal end of the rotating endoscope shaft. The probe also includes a control handle for controlling the imaging controls and a rotation tube that extends through the rotating endoscope shaft and into the control handle. The rotating shaft rotates relative to, and independently of, the control handle. Preferably, the rotating shaft is rotated via a rotation control wheel. The rotation control wheel is fastened or bonded to the rotating tube so that manual rotation of the control wheel causes the rotation tube to rotate, and therefore, the rotating shaft to rotate. Because the rotating endoscope shaft rotates, an imaging element located on, or within, the rotating shaft also rotates.

20 Claims, 4 Drawing Sheets

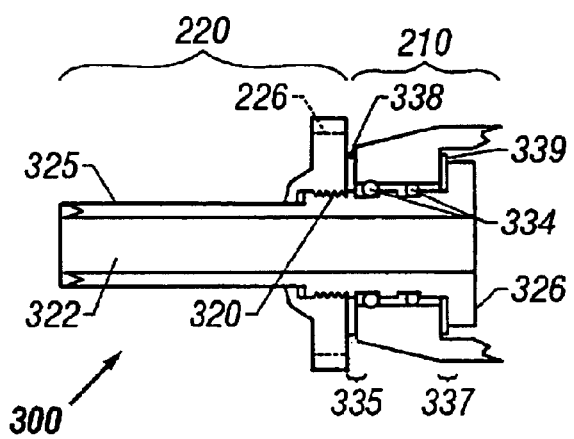
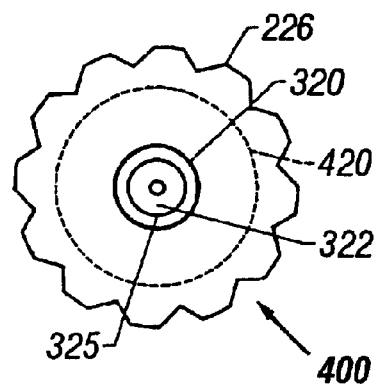
FIG. 3   FIG. 4
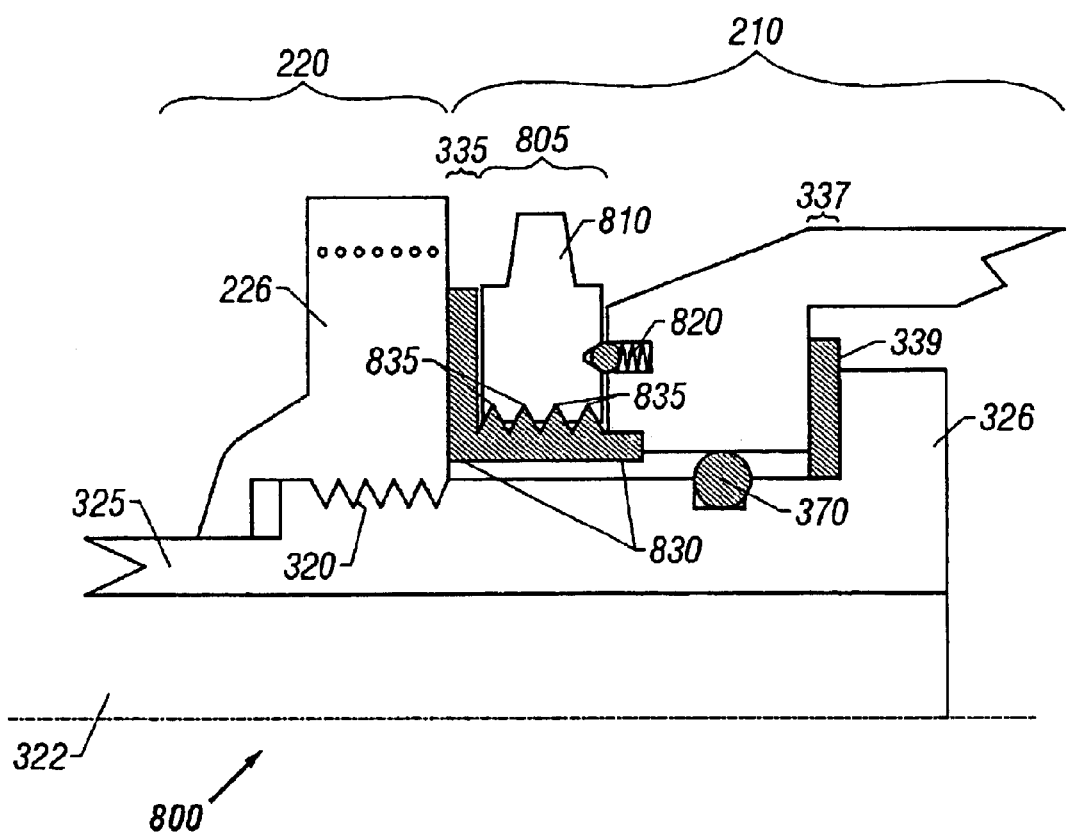
FIG. 5

TRANSESOPHAGEAL ULTRASOUND PROBE HAVING A ROTATING ENDOSCOPE SHAFT

RELATED APPLICATIONS

This application is a Continuation of Ser. No. 09/681,296, filed Mar. 14, 2001 now abandoned.

BACKGROUND OF THE INVENTION

A preferred embodiment of the present invention generally relates to transesophageal probes, and more particularly relates to an improved transesophageal ultrasound probe having a rotating endoscope shaft.

Various medical conditions affect internal organs and structures. Efficient diagnosis and treatment of these conditions typically require a physician to directly observe a patient's internal organs and structures. For example, diagnosis of various heart ailments often requires a cardiologist to directly observe affected areas of a patient's heart. Instead of more intrusive surgical techniques, ultrasound imaging is often utilized to directly observe images of a patient's internal organs and structures.

Transesophageal Echocardiography (TEE) is one approach to observing a patient's heart through the use of an ultrasound transducer. TEE typically includes a probe, a processing unit, and a monitor. The probe is connected to the processing unit which in turn is connected to the monitor. In operation, the processing unit sends a triggering signal to the probe. The probe then emits ultrasonic signals into the patient's heart. The probe then detects echoes of the previously emitted ultrasonic signals. Then, the probe sends the detected signals to the processing unit which converts the signals into images. The images are then displayed on the monitor. The probe typically includes a semi-flexible endoscope that includes a transducer located near the end of the endoscope.

Typically, during TEE, the endoscope is introduced into the mouth of a patient and positioned in the patient's esophagus. The endoscope is then positioned so that the transducer is in a position to facilitate heart imaging. That is, the endoscope is positioned so that the heart or other internal structure to be imaged is in the direction of view of the transducer. Typically, the transducer sends ultrasonic signals through the esophageal wall that come into contact with the heart or other internal structures. The transducer then receives the ultrasonic signals as they bounce back from various points within the internal structures of the patient. The transducer then sends the received signals back through the endoscope typically via wiring. After the signals travel through the endoscope, the signals enter the processing unit typically via wires connecting the endoscope to the processing unit.

Often, in addition to the heart, it may be desirable to image other internal structures within the body of a patient. Imaging other internal structures may require re-positioning of the probe in order to view the internal organs. Additionally, viewing the heart and/or other internal structures from various angles and perspectives may require re-positioning of the probe.

FIG. 1 illustrates a conventional transesophageal ultrasound probe 100 according to one embodiment of the prior art. The probe 100 includes a control handle 110, a fixed endoscope shaft 120 fastened to the distal end of the control handle 110, and a system cable 130 attached to the proximal end of the control handle 110. The fixed endoscope shaft 120 includes a scanhead 122 located at the distal end of the fixed endoscope shaft 120. The scanhead 122 includes an imaging element 124, such as a transducer (not shown). The control handle 110 includes imaging controls 112 mounted on the control handle 110. The imaging controls 112 include imaging control wheels 114 and scan plane push buttons 116 that control the orientation of the scanhead 122. The imaging element 124 is connected to a processing unit (not shown) via wiring (not shown) that extends through the scanhead 122 and throughout the length of the body of the probe 100. The wiring in the probe 100 is then connected via the system cable 130 to the processing unit. The processing unit is then connected via wiring to a monitor (not shown) for display of the image.

In operation, the fixed endoscope shaft 120 of the probe 100 is introduced into the esophagus of a patient. The fixed endoscope shaft 120 is then positioned via the control handle 110 so that the internal structure to be imaged is within the field of view of the imaging element 124 located on, or within, the scanhead 122. Typically, the probe 100 is axially rotated to position the desired internal structure in the field of view of the imaging element 124. In order to rotate the endoscope shaft 120, the entire probe 100 must be rotated. That is, the control handle 110 must be rotated so that the imaging element 124 may image internal structures from different angles and perspectives. For example, to rotate the direction of view 124 of the imaging element of the scanhead 122 by 30°, the control handle 110 typically needs to be rotated 30° because the fixed endoscope shaft 120 is firmly fixed to the control handle 110. Thus, the fixed endoscope shaft 120 is not allowed to rotate independently of the control handle 110. Therefore, as the control handle 110 is rotated by 30°, the imaging controls 122 will also be rotated by 30°. Unfortunately, rotating the imaging controls 122 often may cause confusing and/or counter-intuitive operation of the probe 100. That is, because the imaging controls 112 are fixed, it may be difficult or impossible for an operator to obtain the images he/she desires. Further, observing the resulting images from the physically rotated probe may be confusing. The confusion may lead to misdiagnosis, risks of injury and/or increased time to perform the imaging procedure.

Therefore, a need has existed for a transesophageal ultrasound probe that provides greater and easier access to images of a patient's internal structures. Further, a need has also existed for a transesophageal ultrasound probe that facilitates more intuitive imaging of internal structures from various angles and perspectives.

SUMMARY OF THE INVENTION

The present invention relates to an internal imaging probe for use in a medical imaging system. The probe includes a rotating shaft, such as a rotating endoscope shaft, having an imaging element, such as a transducer, mounted on the distal end of the rotating shaft. The probe also includes a control handle for controlling the imaging element. Preferably, a rotating tube within the probe extends through the rotating shaft into the control handle. The rotation of the rotating tube causes the rotating shaft to rotate. The rotating shaft rotates relative to, and independently of, the control handle to which it is connected. Washers and O-rings provide low friction connections between the rotating tube located in the probe and the control handle.

Preferably, the rotating shaft is rotated via a rotation control wheel located at the distal end of the control handle. The rotation control wheel is fastened or bonded to the rotating tube so that manual rotation of the control wheel causes the rotating tube, and therefore the rotating shaft, to rotate. Because the rotating shaft rotates, an imaging element located on, or within, the rotating shaft also rotates. The rotating shaft may also be set in a locked position so that the rotating shaft may be configured, or preset, to various rotated positions.

Alternatively, the rotation of the rotating shaft may be fully automated. The automated probe may include a motor fixed to a fixed portion of the shaft, or to the control handle. The motor also includes a driving cog wheel, or gear system, that operatively engages a driven cog wheel, or gear system, attached to a rotating portion of the shaft. The rotation of the rotating shaft may then be controlled by levers, potentiometers, or other such devices located on the control handle.

BRIEF DESCRIPTION OF THE DRAWINGS

FIG. 3 illustrates a transverse cross-sectional view of the transesophageal ultrasound probe of FIG. 2 according to a preferred embodiment of the present invention.

FIG. 4 illustrates an axial cross-sectional view through the rotation control wheel of the transesophageal ultrasound probe of FIG. 2 according to a preferred embodiment of the present invention.

FIG. 5 illustrates a transverse cross-sectional view of the transesophageal ultrasound probe of FIG. 2 with a braking mechanism according to an alternative embodiment of the present invention.

DETAILED DESCRIPTION OF THE INVENTION

Figure 1:
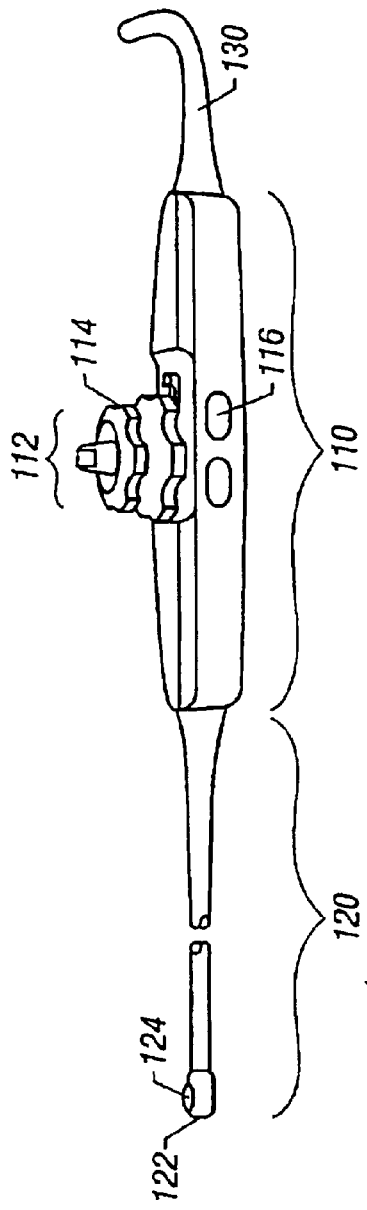
FIG. 1 illustrates a conventional transesophageal ultrasound probe according to one embodiment of the prior art.

The foregoing summary, as well as the following detailed description of the preferred embodiments of the present invention, will be better understood when read in conjunction with the appended drawings. For the purpose of illustrating the invention, there are shown in the drawings, embodiments which are presently preferred. It should be understood, however, that the present invention is not limited to the precise arrangements and instrumentality shown in the attached drawings.

Figure 2:
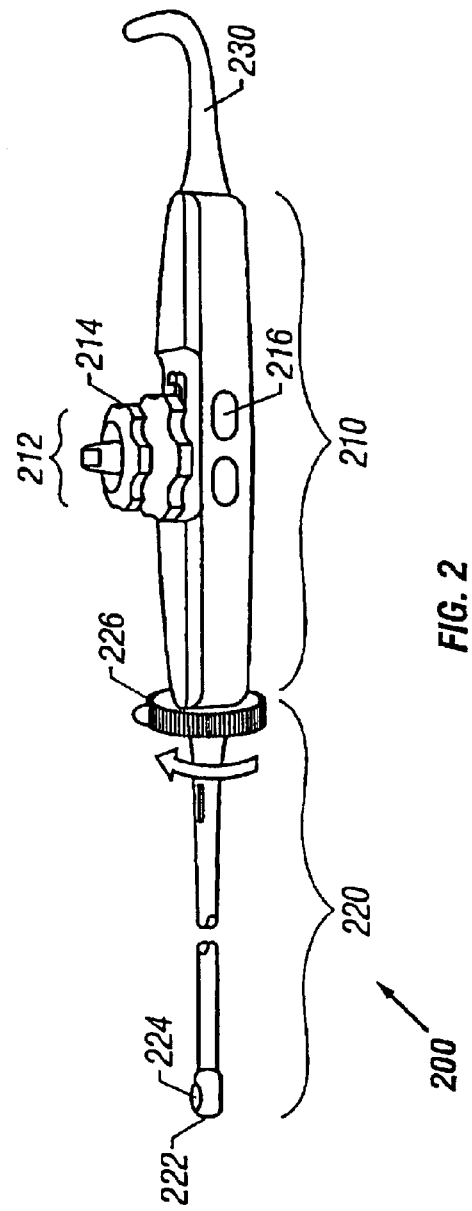
FIG. 2 illustrates a transesophageal ultrasound probe according to a preferred embodiment of the present invention.

FIG. 2 illustrates a transesophageal ultrasound probe 200 according to a preferred embodiment of the present invention. The probe 200 includes a control handle 210, a rotating endoscope shaft 220 extending from the control handle 210, and a system cable 230 connecting the control handle 210 to a processing unit (not shown). The control handle 210 includes imaging controls 212 mounted on the control handle 210. The imaging controls 212 include imaging control wheels 214 and scan plane push buttons 216 for controlling the movement of an imaging element 224 located on, or within, the distal end of the imaging probe 200. The rotating endoscope shaft 220 includes a scanhead 222. The scanhead 222 includes the imaging element 224, such as a transducer. Preferably, the imaging element is located at the distal end of the rotating endoscope shaft 220. Additionally, the rotating endoscope shaft 220 includes a rotation control wheel 226 fastened to the rotating shaft 220 and located at the distal end of the control handle 210.

FIG. 3 illustrates a transverse cross-sectional view 300 of the transesophageal ultrasound probe 200 of FIG. 2 according to a preferred embodiment of the present invention. The cross sectional view 300 includes the control handle 210, the rotating endoscope shaft 220, a rotating tube 325 having an extended proximal end 326, the rotation control wheel 226, a threaded interface 320, an inner cavity 322, a wheel stop area 335, a washer 338, O-rings 334, a tube stop area 337, and a washer 339. The rotating tube 325 extends throughout the body of the rotating shaft 220 and into the control handle 210. The inner cavity 322 is formed within the rotating tube 325. The rotating tube 325 is fastened to the rotation control wheel 226 at the threaded interface 320. The rotation control wheel 226 abuts the wheel stop area 335 via the washer 338. The washer 338 in turn abuts the control handle 210. The control handle 210 is connected to the rotation tube 325 via the O-rings 334. The control handle 210 abuts the tube stop area 337 via the washer 339. The washer 339 in turn abuts the extended proximal end 326 of the rotation tube 325. The washer 338 and O-rings 334 provide a low-friction connection between the control handle 210 and the rotation control wheel 226. Similarly, the washer 339 and O-rings 334 provide a low-friction connection between the control handle 210 and the extended proximal end 326 of the rotation tube 325. Additionally, the O-rings 334 provide a sealing connection between the control handle 210 and the rotating tube 325.

FIG. 4 illustrates an axial cross-sectional view 400 through the rotation control wheel 226 of the transesophageal ultrasound probe 200 of FIG. 2 according to a preferred embodiment of the present invention. FIG. 4 includes the rotation tube 325 defining the inner cavity 322, the threaded interface 320, a reference line 420 illustrating the circumference of the extended control handle 210 and the control wheel 226.

Referring to FIG. 3, the rotating tube 325 is fastened to the control wheel 226 via the threaded interface 320. Preferably, the rotating tube 325 is securely fastened to the rotation control wheel 226 via the threaded interface 320 with a fastening agent, such as glue or some other fastening agent, that forms a fluid-tight seal. The control wheel 226 is separated from the control handle 210 by the washer 338. For example, the washer may be a low friction plastic washer that fits over the rotating tube 325. Alternatively, the washer 338 may be a locking washer. In addition to providing a low friction interface between the rotation control wheel 226 and the control handle 210, the washer 338 also provides a seal between the rotation control wheel 226 and the control handle 210. Additionally, the O-rings 334 form a fluid-tight seal between the control handle 210 and the rotating endoscope shaft 220.

The control handle 210 is separated from the proximal end 326 of the rotating tube 325 by the washer 339. Preferably, the diameter of the proximal end 325 of the rotating tube 325 is greater than the diameter of the internally introduced portion of the rotating tube 325. Preferably, the proximal end 325 of the rotating tube 325 abuts the tube stop area 337 when the probe 200 of FIG. 2 is fully assembled.

During assembly, the rotation control wheel 226 is rotated on the thread of the rotating rube 325 while the rotating tube 325 does not rotate, thus introducing the proximal end 326 of the rotating tube 325 into contact with the tube stop area 337 as the rotation control wheel 226 comes into contact with the wheel stop area 335. The washer 338 cushions and seals a low-friction connection between the rotation control wheel 226 and the control handle 210 as the rotation control wheel 226 and the control handle 210 come together. Similarly, the washer 339 cushions and seals a low-friction connection between the proximal end 326 of the rotation tube 325 and the control handle 210 as the proximal end 326 of the rotation tube 325 and the control handle 210 come together.

Once the rotation control wheel 226 has been rotated to its fullest extent, the rotation control wheel 226 is sealed to the rotating tube 325 at the threaded interface 320. Thus, the washer 338 forms a compressive seal between the rotation control wheel 226 and the control handle 210; and the washer 339 forms a compressive seal between the proximal end 326 of the rotation tube 325 and the control handle 210 at the tube stop area 337. Washers and O-rings may be integrated as part of the rotation control wheel 226, rotating tube 325 or the control handle 210 if necessary. For example, if the rotation control wheel 226 is composed of hard plastic, then the washer 338 may not be necessary.

In general, the probe 200 of FIG. 2 may be included in a medical imaging system. Such a medical imaging system may include the probe 200, a processing unit (not shown), and a monitor (not shown). In operation, an internal structure is imaged by the probe 200 and the resultant image is sent to the processing unit for processing and display on the monitor.

Referring again to FIG. 2, in operation, the rotating endoscope shaft 220 is introduced into the patient's esophagus via the patient's mouth in a similar fashion as that of the conventional probe 100 of FIG. 1. Once the rotating endoscope shaft 220 is introduced, the rotating endoscope shaft 220 is positioned such that an internal structure to be imaged is within the field of view of the imaging element 224. The imaging element 224, such as a transducer, located within the scanhead 222 is controlled via the imaging controls 212 located on the control handle 210. The imaging element 224 is connected to the imaging controls 212 via wiring (not shown) within the inner cavity 322 of the probe 200. During imaging, the imaging element 224 of the scanhead 222 sends and receives signals through wiring (not shown) located within the inner cavity 322 of the imaging probe 200 to a processing unit (not shown) via the system cable 230. The processing unit receives the signals via the system cable 230, which is in turn connected to wiring located within the probe 200.

During imaging, the rotating endoscope shaft 220 may be rotated relative to, and independent of, the control handle 210. That is, the control handle 210 may remain in one orientation while the rotating endoscope shaft 220 is rotated about an axis that is common to both the rotating endoscope shaft 220 and the control handle 210. In order to rotate the rotating endoscope shaft 220 about the common axis, the rotation control wheel 226 is turned. Because the rotating tube 325 is fastened to the rotation control wheel 226, rotation of the rotation control wheel 226 causes a corresponding rotation in the rotating tube 325. The rotation of the rotating tube 325 causes the rotating endoscope shaft 220 to rotate. The independent rotation of the rotating endoscope shaft 220 allows the control handle 210 to remain in the same orientation throughout the imaging process while the rotating endoscope shaft 220 rotates to allow the imaging element 224 of the scanhead 222 to image internal structures from different angles and perspectives.

Optionally, the rotating endoscope shaft 220 may be set, or locked, into position at any point throughout its rotation by a locking mechanism (not shown). The locking mechanism may be controlled via the rotation control wheel 226, or additional controls located on the control handle 210. For example, the rotating endoscope shaft 220 may be locked, or set, into a position corresponding to a position that is comfortable and intuitive to a particular physician, cardiologist, or other user of the probe 200. For example, an individual may prefer to position the imaging element 224 fixed to the rotating endoscope shaft 220 at a 30° radial rotation with respect to the imaging controls 212 positioned on the control handle 210 before, and throughout, the imaging process. Alternatively, the rotation of the rotating endoscope shaft 220 may be sufficiently stiff so that a locking mechanism is not necessary.

Also, a physical end-stop may be located on the proximal end 326 of the rotating tube 325. The end-stop may limit the rotation of the rotating tube 325 and therefore, the rotating endoscope shaft 220, to 180° or less in order to prevent twisting the various wires and cables (not shown) located in the inner cavity 322 of the probe 220. The end-stop may be a pin, block, notch, or other stopping mechanism attached to the proximal end 326 of rotating tube 325 that comes into contact with another pin, block, notch, or other stopping mechanism, attached to the interior of the control handle 210.

FIG. 5 illustrates a transverse cross-sectional view 800 of the transesophageal ultrasound probe 200 of FIG. 2 with a low friction braking mechanism 805 according to an alternative embodiment of the present invention. The cross-sectional view 800 includes the control handle 210, the rotating endoscope shaft 220, the rotating tube 325 having the extended proximal end 326, the rotation control wheel 226, the threaded interface 320, the inner cavity 322, the wheel stop area 335, a single O-ring 370, the tube stop area 337, the washer 339, and a low friction braking mechanism 805. The braking mechanism 805 includes a brake handle 810, a brake limit 820, an flanged cylinder brake 830, and a series of threads 835 between the brake handle 810 and the brake 830. The low friction washer 338 of FIG. 3 is replaced by the low friction braking mechanism 805. The brake 830 is threadably fastened onto the rotating braking handle 810 via the threads 835. The brake limit 820 is preferably a spring-ball configuration that limits, or restricts, the rotation of the brake handle 810. The brake limit 820 is positioned within the main body of the control handle 210 and extends into the rotating braking handle 810.

In operation, the brake handle 810 is engaged to brake, or lock, the rotation of the rotating tube 325. Preferably, the brake handle 810 is rotated to brake the rotating tube 325. Because the brake 830 is threadably fastened onto the brake handle 810, the brake 830 moves linearly towards, or away from, the rotation control wheel 226 as the brake handle 810 is rotated. As the brake handle 810 rotates in a locking direction, the brake 830 is compressed into the rotation control wheel 226. The brake 830 brakes the rotation control wheel 226 as the brake 830 is compressed into the rotation control wheel 226. As the rotation of the rotation control wheel 226 is braked, the rotation of the rotating tube 325 is also braked. The brake limit 820 limits the rotation of the brake handle 810. For example, the brake limit 820 may include pre-defined locked positions that stop the rotation of the brake handle 810 as the brake handle 810 rotates into one of the locked positions. As the brake handle 810 rotates away from the locking direction, thereby disengaging the brake 830, the brake 830 moves away from the rotation control wheel 226. As the brake 830 is disengaged, the rotation control wheel 226 is able to rotate; thus, the rotating tube 325 is able to rotate.

Alternatively, the brake mechanism 805 may include a screw that may be positioned perpendicular to the surface of the rotating tube 325 via a threaded hole in the control handle 210. As the screw is engaged, the screw moves toward the rotating tube 325. The screw restricts the rotation of the rotating tube 325 as the screw is threaded through the control handle 210 towards, and into, the rotating tube 325. The rotating tube 325 may include notches that may receive the screw. As the screw enters the notches on the rotating tube 325, the rotation of the rotating tube is restricted.

Alternatively, the rotation of the rotating endoscope shaft 220 may be controlled in various ways. For example, the probe 200 may be fully automated. That is, the rotation of the rotating endoscope shaft 220 may be controlled through the use of motors, gears, and/or cog wheels.

Figure 6:
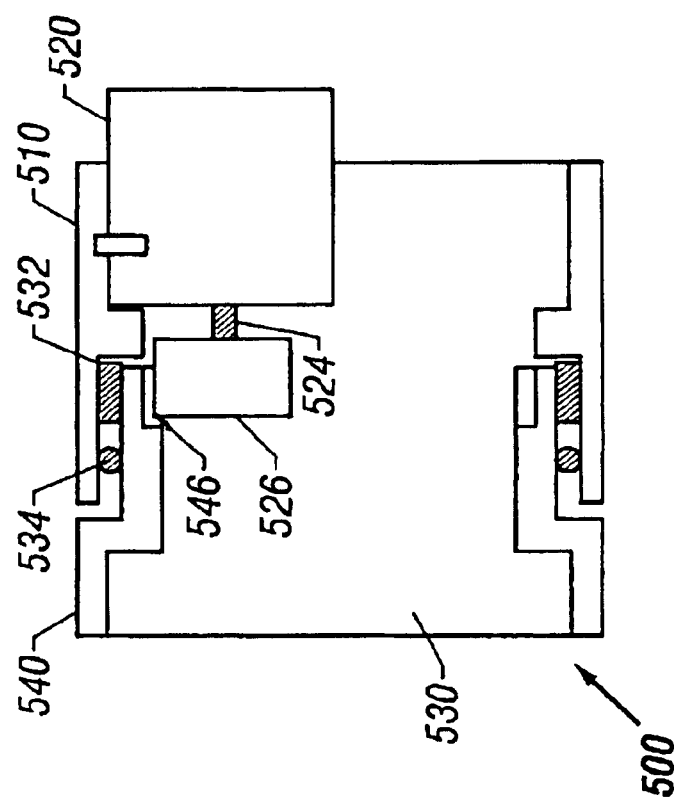
FIG. 6 illustrates a transverse cross-sectional view of a transesophageal ultrasound probe segment according to an alternative embodiment of the present invention.

FIG. 6 illustrates a transverse cross-sectional view of a transesophageal ultrasound probe segment 500 according to an alternative embodiment of the present invention. The transverse cross-sectional view includes a fixed endoscope shaft 510, a rotating shaft 540, bearings 532, an inner cavity 530, and an O-ring 534. The fixed endoscope shaft 510 includes a motor 520 mounted to the interior of the fixed endoscope shaft 510. The motor 510 includes an axle 524 extending toward the distal end of the probe segment 500 and a driving cog wheel 526 attached at the opposite end of the axle 524 from the motor 510. The rotating shaft 540 includes a driven cog wheel 546 extending into the inner cavity 530. The bearings 532 encircle the fixed endoscope shaft 510 and provide a low-friction connection between the fixed endoscope shaft 510 and the rotating shaft 540. The inner cavity 530 is formed within the probe segment 500 and extends through the fixed endoscope shaft 510 and the rotating shaft 540. The O-ring 534 encircles the fixed endoscope shaft 510 and provides a fluid-tight seal between the fixed endoscope shaft 510 and the rotating shaft 540.

Figure 7:
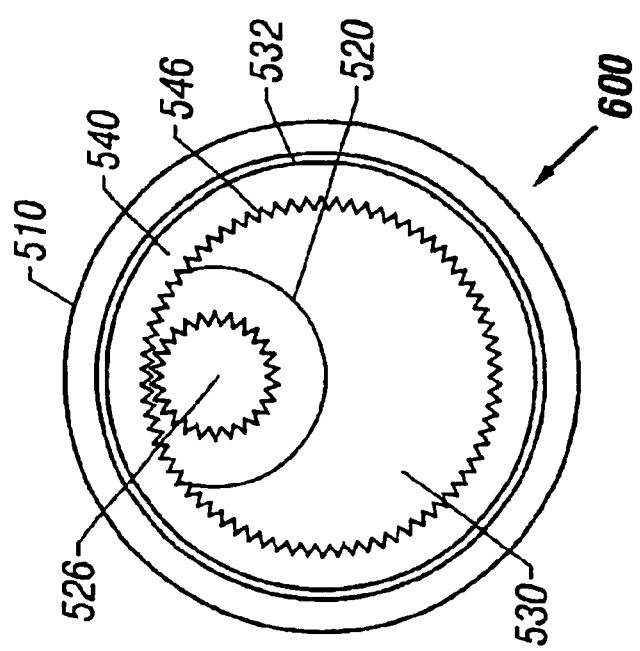
FIG. 7 illustrates an cross-sectional axial view of the transesophageal ultrasound probe segment of FIG. 6 according to an alternative embodiment of the present invention.

FIG. 7 illustrates an axial cross-sectional view 600 of the transesophageal ultrasound probe segment 500 of FIG. 6 according to an alternative embodiment of the present invention. The cross-sectional axial view 600 includes the fixed endoscope shaft 510, the motor 520, the driving cog wheel 526, the inner cavity 530, the bearing 532, the rotating shaft 540 and the driven cog wheel 546.

In operation, the rotating shaft 540 is engaged by controls (not shown), such as buttons, levers, or potentiometers, located on the control handle 210. The motor 520 is electrically connected to the controls via wiring. When activated, the motor 520 rotates the axle 524, which in turn, rotates the driving cog wheel 526. The driving cog wheel 526 operatively engages the driven cog wheel 546. Therefore, as the driving cog wheel 526 rotates, the driven cog wheel 546 rotates in the same direction as that of the driving cog wheel 526. The rotation of the driven cog wheel 546 in turn causes the rotating shaft 540 to rotate in the same direction as that of the driven cog wheel 546. The scanhead 222 located on the distal end of rotating shaft 540 therefore rotates as the rotating shaft 540 rotates.

The interface between the rotating shaft 540 and the fixed endoscope shaft 510 may be located at various points of the probe segment 500. For example, the interface between the rotating shaft 540 and the fixed endoscope shaft 510 may be located near the control handle 210, near the scanhead 222, or positioned at various points between the control handle 210 and the scanhead 222. Alternatively, the fixed endoscope shaft 510 may be part of the control handle 210 of the probe 200 of FIG. 2. Thus, the motor 520 may be attached to the interior of the control handle 210.

Figure 8:
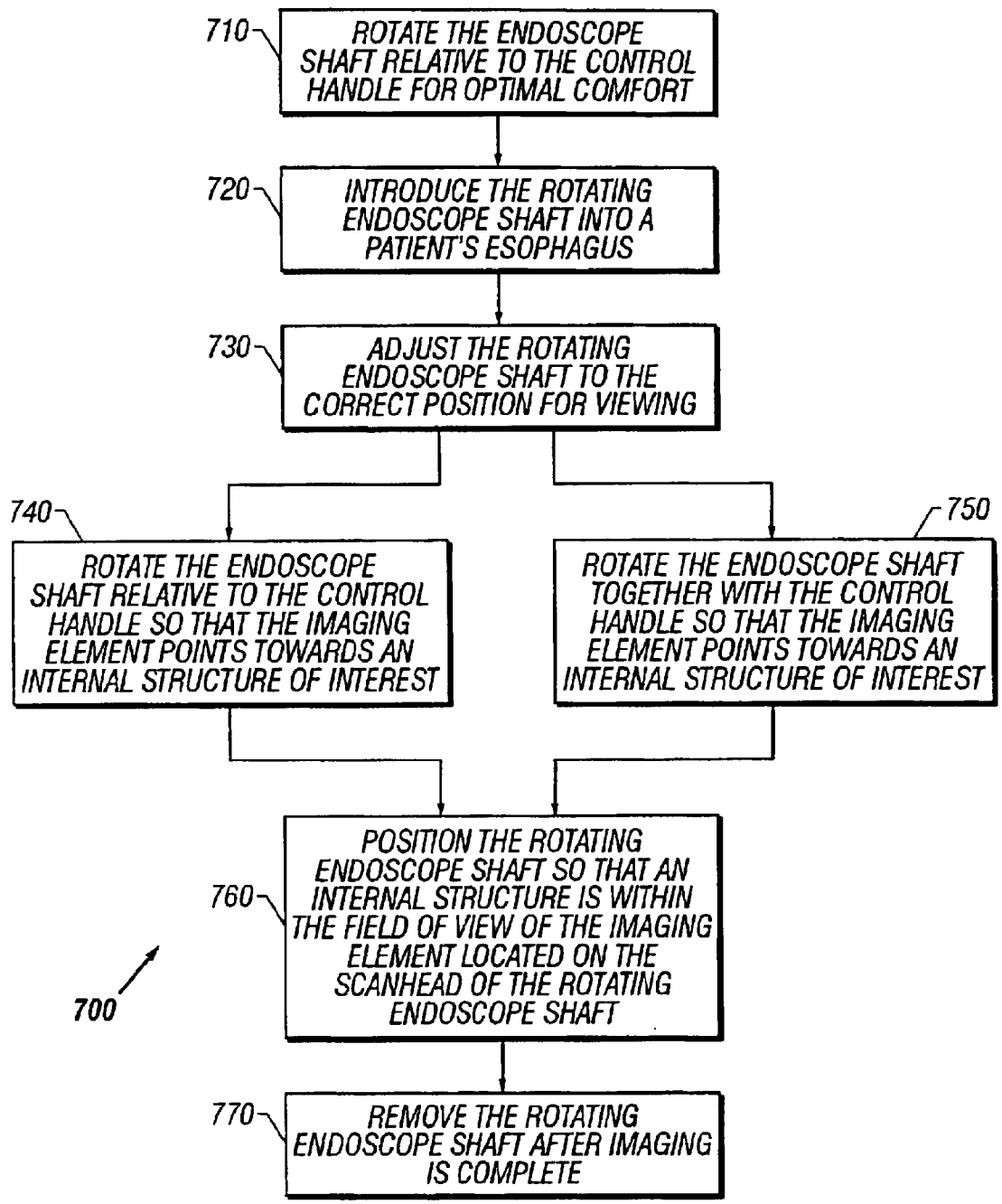
FIG. 8 illustrates a flow chart of a preferred embodiment of the present invention.

FIG. 8 illustrates a flow chart 700 of a preferred embodiment of the present invention. First, at step 710, a physician rotates the endoscope shaft 220 relative to the control handle 210 to suit the physician's preference. That is, the physician rotates the endoscope shaft 220 at step 710 for optimal comfort. Next, at step 720, the physician introduces the rotating endoscope shaft 220 into a patient's esophagus. The physician then adjusts, or positions, the rotating endoscope shaft 220 to a suitable position for viewing at step 730. That is, the physician adjusts, or positions, the rotating endoscope shaft 220 to a suitable position for viewing a particular internal structure.

The physician then rotates the endoscope shaft 220 so that the imaging element 224 points towards an internal structure of interest. The physician may either rotate the endoscope shaft 220 relative to the control handle 210 via the rotation control wheel 226 at step 740, or the physician may rotate the endoscope shaft 220 together with the control handle 210. Next, at step 760, the physician positions the rotating endoscope shaft 220 so that an internal structure to be imaged is within the field of view of the imaging element 224 located on the scanhead 222 of the rotating endoscope shaft 220. At step 760, the rotating endoscope shaft 220 is positioned via imaging controls 212 or other controls on the control handle 210 so that an internal structure is within the field of view of the imaging element 224 located on the scanhead 222. After the physician positions the rotating endoscope shaft 220 so that an internal structure is within the field of view of the imaging element 224, the internal structure is imaged. Finally, at step 770, the physician removes the rotating endoscope shaft 220 from the esophagus of the patient after imaging is complete.

Alternatively, the physician may rotate the rotating endoscope shaft 220 via the rotation control wheel 226 during the imaging process to view different internal structures within the body of the patient. Also, the physician may rotate the rotating endoscope shaft 220 via the rotation control wheel 226 during the imaging process to view the original internal structure from a different perspective.

Thus the present invention provides an improved transesophageal ultrasound probe that provides greater and easier access to images of internal structures within a patient because the probe includes a rotating shaft that rotates independently of the probe's control handle. The independent rotation of the rotating shaft provides greater imaging access. Further, the transesophageal ultrasound probe having a rotating endoscope shaft facilitates more intuitive images of internal structures from various angles and perspectives. Additionally, various other imaging methods, such as live video, may be used with the present invention. Also, the present invention is not limited to imaging. For example, the present invention may also be utilized in surgical applications such as trans-rectal prostate treatment.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed:

1. An internal imaging probe including:
   a rotating endoscope shaft having an imaging element;
   a control handle;
   a rotating tube extending throughout the body of said rotating endoscope shaft into said control handle; and
   a rotation control affixed to said rotating tube,
   said rotation control for rotating said imaging element relative to said control handle.

2. The probe of claim 1 further including at least one washer located between said rotating tube and said control handle for decreasing friction between said rotating tube and said control handle.

3. The probe of claim 1 further including at least one O-ring forming a seal between said rotating tube and said control handle.

4. A medical imaging system including a probe for imaging internal structures of a patient, said probe including:
   a rotating endoscope shaft having an imaging element;
   a control handle;
   a rotating tube extending throughout the body of said rotating endoscope shaft into said control handle; and
   a rotation control contacting said rotating tube,
   said rotation control for rotating said imaging element relative to said control handle.

5. The system of claim 4 further including at least one washer located between said rotating tube and said control handle for decreasing friction between said rotating tube and said control handle.

6. The system of claim 4 further including an O-ring forming a seal between said rotating tube and said control handle.

7. A system for imaging internal structures of a patient including an internal imaging probe including:
   a rotating endoscope shaft having an imaging element;
   a control handle;
   a rotating tube extending throughout the body of said rotating endoscope shaft into said control handle; and
   a rotation control affixed to said rotating tube;
   said rotation control located at the distal end of said control handle, and said rotation control operable to rotate said imaging element relative to said control handle.

8. The system of claim 7 wherein said probe is a transesophageal echocardiography probe.

9. The system of claim 7 further including at least one washer located between said rotating tube and said control handle for decreasing the friction between said rotating tube and said control handle.

10. The system of claim 7 further including an O-ring forming a seal between said rotating tube and said control handle.

11. The system of claim 7 wherein said imaging element is a transducer.

12. The system of claim 7 wherein said control handle includes imaging controls for controlling said imaging element.

13. The system of claim 7 further including a braking mechanism, said braking mechanism including:
   a brake;
   a brake handle threadably fastened to said brake; and
   a brake limit restricting said brake handle, said brake handle rotating to linearly move said brake towards said rotation control.

14. The system of claim 7 further including a braking mechanism having a screw, said braking mechanism threading said screw into a rotation tube of said rotating shaft to restrict the rotation of said rotating shaft.

15. An internal imaging system including:
   a rotating endoscope shaft having an imaging element;
   a fixed endoscope shaft;
   a motor fixed to said fixed endoscope shaft;
   a driving cog wheel attached to said motor; and
   a driven cog wheel attached to said rotating endoscope shaft, said driving cog wheel operatively engaging said driven cog wheel to rotate said rotating endoscope shaft relative to said fixed endoscope shaft.

16. The system of claim 15 further including a bearing located between said fixed endoscope shaft and said rotating endoscope shaft for decreasing the friction between said fixed endoscope shaft and said rotating endoscope shaft.

17. The system of claim 15 further including an O-ring forming a seal between said rotating endoscope shaft and said control handle.

18. The system of claim 15 wherein said imaging element is a transducer.

19. The system of claim 15 wherein said control handle includes imaging controls for controlling said imaging element.

20. An internal imaging probe including:
   a rotating tube having an imaging element;
   a control handle;
   a rotation control operable to rotate said imaging element relative to said control handle;
   a brake;
   a brake handle fastened to said brake; and
   said brake handle operating to move said brake, wherein said brake restricts rotation of said rotating tube.

* * * * *